US00PP10021P

United States Patent [19]

Lemon

[11] Patent Number: Plant 10,021

[45] Date of Patent: Sep. 2, 1997

[54] GERANIUM PLANT NAMED 'ERIN'

[75] Inventor: David Lemon, Lompoc, Calif.

[73] Assignee: John Bodger and Sons Company, South El Monte, Calif.

[21] Appl. No.: 571,203

[22] Filed: Dec. 12, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 7,467 3/1991 Craig et al. ..... Plt./87.12

P.P. 8,091 1/1993 Walters ..... Plt./87.12

*Primary Examiner*—Howard J. Locker

*Attorney, Agent, or Firm*—Fulwider, Patton, Lee & Utecht, LLP

[57] ABSTRACT

The cultivar is characterized by its clean, deep pink color. Its compact, controlled growth habit and prolific blooms provide for superb cuttings and performs equally well in hanging baskets or as a pot plant. The blooms continue for 8 to 10 weeks in the greenhouse.

1 Drawing Sheet

BACKGROUND OF THE NEW PLANT

The present invention comprises a new and distinct cultivar of *Pelargonium×domesticum* known by the varietal name Erin (Oglevee No. 57, Bodger No. 8PD 37-1). The new variety was discovered in a selective breeding program by David Lemon at Bodger Seeds, Ltd., Lompoc, Calif. The new variety is a selection from the crossing of Olga (unpatented) ×Hazel Harmony (unpatented). Olga has light orchid flowers and light green leaves, whereas Erin has salmon pink flowers and medium dark leaves. Hazel Harmony is a lavender bicolor variety.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light 60° Fahrenheit night temperature, 68° Fahrenheit day temperature, 72° Fahrenheit vent temperature and grown in a soilless media of constant fertilizer 150 to 200 parts per million of nitrogen and potassium has a response time of fourteen (14) weeks from the rooted cutting to a flowering plant in a 15.0 cm pot.

cl DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings potted on Nov. 1, 1993 and flowered Feb. 10, 1994 under full light and greenhouse, and colorings were taken indoors under 200–220 foot candles of fluorescent cool white light using the R.H.S. Colour Chart of The Royal Horticultural Society of London.

THE PLANT

Classification:

*Botanical.*—*Pelargonium×domesticum.*

Form: Upright; mounted habit.

Height.—20.0 cm from the media surface.

*Growth.*—Free flowering; good basal branching.

*Strength.*—Quick rooting, prolific flowering, artificial support not needed.

Foliage: Stalked leaf attachment.

Leaves:

*Size.*—7.0–9.0 cm across.

*Shape.*—Depressed ovate; truncate base.

*Margin.*—Serratedly lobed.

*Texture.*—Leathery; slightly reflective.

*Color.*—Top: Green Group 137B; Zone: Not Present; Bottom: Yellow/green Group 147B.

*Ribs and veins.*—Palmate venation: Color: Yellow/Green group 147C.

Petioles:

*Length.*—4.0–6.0 cm.

*Color.*—Yellow/Green Group 146C.

Stem:

*Color.*—Yellow/green group 146C.

*Internodes.*—1.0–2.5 cm in length.

THE BUD

Shape: Elliptical.

Size: 1.5–2.0 cm across; bud just beginning to show color.

INFLORESCENCE

Blooming habit: Many large florets opening into a full flower head.

Size: 9.0–11.0 cm across — fully open bloom.

Born: Umbel, florets on pedicel; pedicel on peduncle; 6.0–8.0 cm above foliage.

Florets:

*Form.*—Cupped.

*Color.*—Top: Red/Purple Group 58D; Bottom: Red Group 56D; Eye: White with a feather of Red/Purple Group 64A; Upper petal markings: R.H.S. 64A; Margin Color: R.H.S. 58D; Region between margin and markings: R.H.S. 61C; Lower petal markings: R.H.S. 64A.

*Petals.*—5–7 cm in number; single, not united; margin entire.

*Size.*—5.0–6.5 cm across when fully open.

*Texture and appearance.*—Smooth and satiny. Appearance from a distance is candy pink bloom flowers above a neat mound of medium green foliage.

Petaloids:

*Quantity.*—None present.

Pedicel:

*Length.*—1.5–2.5 cm.

*Color.*—Yellow/Green Group 146C.

Peduncle:

*Length.*—6.0–9.0 cm in length.

*Color.*—Yellow/Green Group 146C.

Persistence:

*Disease resistance.*—Not known.

*Lasting quality.*—Blooms will last 21–25 day in a home environment.

REPRODUCTIVE ORGANS

Stamens:

*Anthers.*—2.0–3.0 mm in length.

*Filaments.*—1.5–1.8 cm in length; white.

*Pollen*—Golden Brown.

Pistils:

*Number.*—One.

*Length.*—1.5–1.8 cm.

*Stigma.*—One; 5–6 parted, Red/Purple in color.

*Style.*—1.0 cm in length.

Ovaries: Superior, pubescent; pale green in color, 5.0–7.0 mm in length.

Fruit: None observed.

GENERAL CHARACTERISTICS

This new Geranium variety, Erin, is an improvement on the current Regal variety Allure (U.S. Plant Pat. No. 7,467). The flower color is a cleaner and deeper pink than Allure. The plant form is more controlled with abundant cuttings.

For production purposes, Erin is a very good cutting producer and is very easy to root. Erin can be used in either hanging baskets or as a pot plant and will be a very prolific bloomer.

I claim:

1. A new and distinct variety of geranium plant, substantially as shown and described.

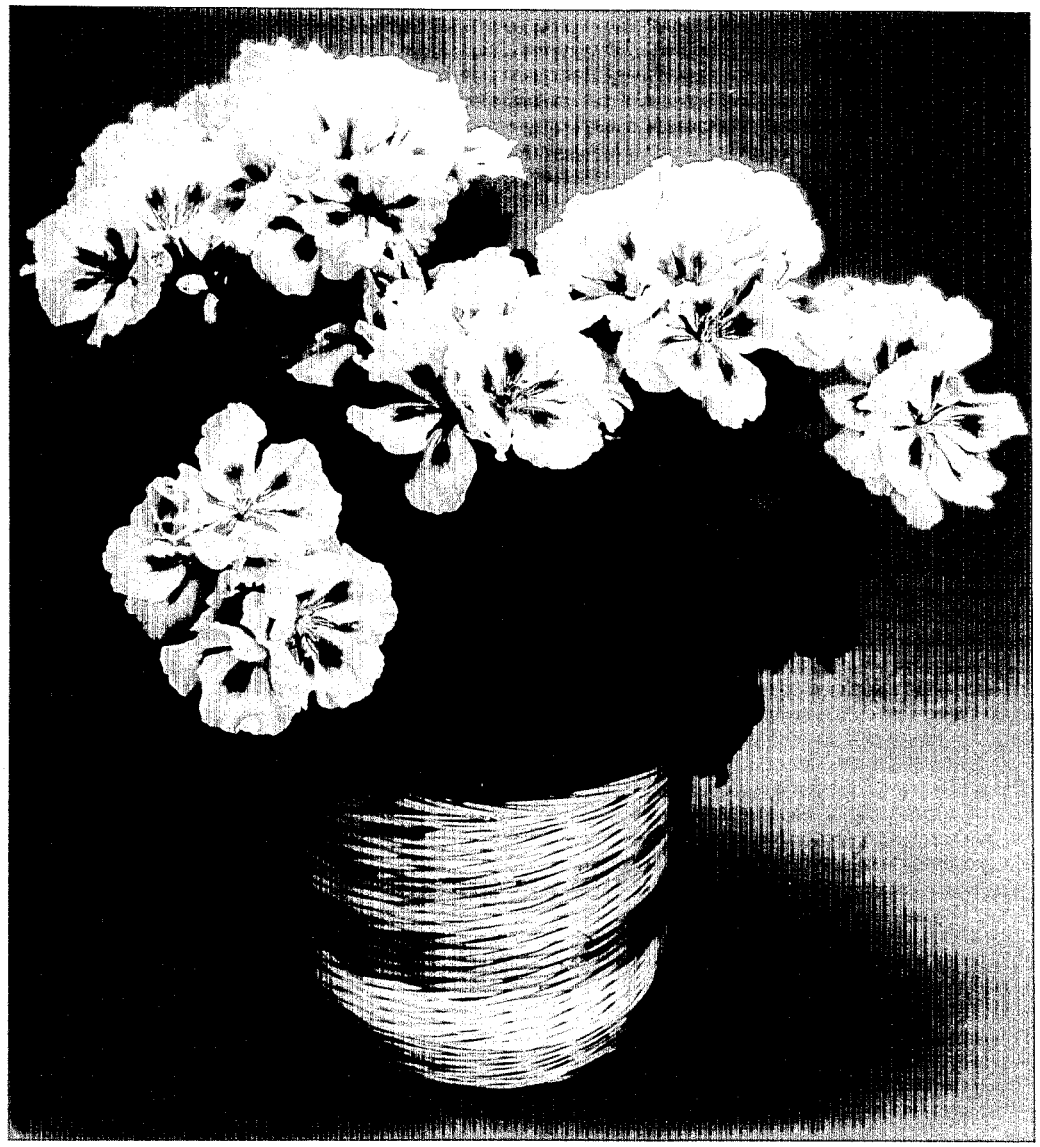

* * * * *